US008990048B2

(12) United States Patent
Czaja et al.

(10) Patent No.: US 8,990,048 B2
(45) Date of Patent: Mar. 24, 2015

(54) ADAPTIVE SKI BINDINGS SYSTEM

(71) Applicant: IPComm LLC, Cardiff, CA (US)

(72) Inventors: Stanislaw Czaja, Cardiff, CA (US); Andrzej Bachleda-Curus, Zakopane (PL); Ilona Stawski, Avon Lake, OH (US); Muhammad Afsar, San Diego, CA (US)

(73) Assignee: IPComm, Cardiff, CA (US)

( * ) Notice: Subject to any disclaimer, the term of this patent is extended or adjusted under 35 U.S.C. 154(b) by 0 days.

(21) Appl. No.: 14/107,223

(22) Filed: Dec. 16, 2013

(65) Prior Publication Data

US 2014/0257568 A1     Sep. 11, 2014

Related U.S. Application Data

(63) Continuation-in-part of application No. 13/024,070, filed on Feb. 9, 2011, now Pat. No. 8,612,181.

(51) Int. Cl.

| G06F 19/00 | (2011.01) |
|---|---|
| A63C 9/00 | (2012.01) |
| A43B 3/00 | (2006.01) |
| A43B 5/04 | (2006.01) |
| A63C 5/06 | (2006.01) |
| G05D 19/02 | (2006.01) |

(52) U.S. Cl.
CPC .................. *A63C 9/00* (2013.01); *A43B 3/0005* (2013.01); *A43B 5/0415* (2013.01); *A63C 5/06* (2013.01); *G05D 19/02* (2013.01); *A63C 2203/18* (2013.01); *A63C 2203/22* (2013.01); *G06F 19/3481* (2013.01)
USPC .................. 702/188; 702/72; 702/19; 702/44; 702/160; 702/141; 702/149; 702/187; 422/101; 422/72; 422/63; 436/43

(58) Field of Classification Search
CPC ...... A63C 9/001; A63C 5/06; A63C 2203/22; A63C 2203/18; A43B 5/0415; A43B 3/0005; G06F 19/3481; G05D 19/02
USPC ............... 702/72, 19, 44, 160, 182, 141, 149, 702/187, 188; 422/101, 72, 63; 436/43
See application file for complete search history.

(56) References Cited

U.S. PATENT DOCUMENTS

| 5,524,637 | A | * | 6/1996 | Erickson ..................... 600/592 |
|---|---|---|---|---|
| 5,862,803 | A | * | 1/1999 | Besson et al. ................ 600/508 |
| 6,498,994 | B2 | * | 12/2002 | Vock et al. ..................... 702/44 |
| 6,631,384 | B1 | * | 10/2003 | Richman et al. ..................... 1/1 |
| 6,885,971 | B2 | * | 4/2005 | Vock et al. ................... 702/182 |
| 6,959,259 | B2 | * | 10/2005 | Vock et al. ................... 702/142 |
| 7,054,784 | B2 | * | 5/2006 | Flentov et al. ............... 702/149 |
| 7,072,789 | B2 | * | 7/2006 | Vock et al. ................... 702/141 |
| 7,092,846 | B2 | * | 8/2006 | Vock et al. ................... 702/182 |
| 7,200,517 | B2 | * | 4/2007 | Darley et al. ................. 702/160 |
| 8,044,772 | B1 | * | 10/2011 | Roe ................................. 340/7.5 |
| 8,239,146 | B2 | * | 8/2012 | Vock et al. ..................... 702/44 |
| 2003/0163287 | A1 | * | 8/2003 | Vock et al. ................... 702/187 |
| 2006/0015287 | A1 | * | 1/2006 | Vock et al. ................... 702/141 |
| 2006/0235642 | A1 | * | 10/2006 | Vock et al. ................... 702/141 |
| 2011/0131012 | A1 | * | 6/2011 | Czaja et al. .................. 702/188 |
| 2012/0262297 | A1 | * | 10/2012 | Poon ............................. 340/584 |

* cited by examiner

*Primary Examiner* — Carol S Tsai

(57) ABSTRACT

System for adaptive control and release of ski bindings comprising a smart-phone based application performing calculation of forces applied to the ski-binding system by analyzing acceleration vectors received from accelerometers embedded in the bindings, then instantaneously releasing both bindings if one or more of the predefined safety thresholds was exceeded.

17 Claims, 15 Drawing Sheets

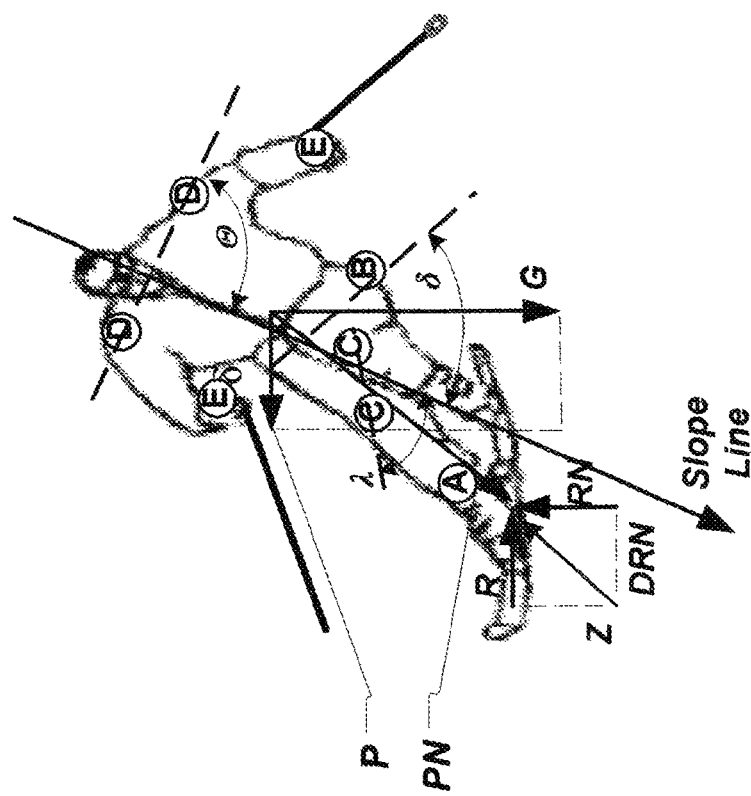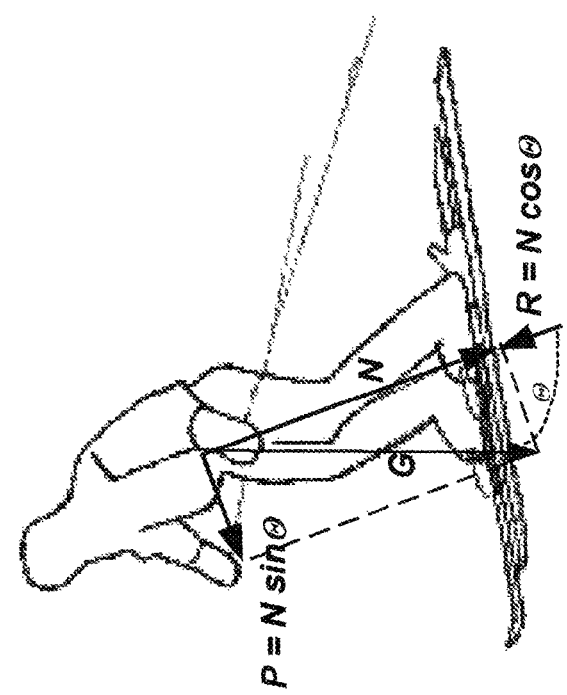
Fig. 6

ADAPTIVE SKI BINDINGS SYSTEM

PRIORITY INFORMATION

This application is a Continuation in Part of application of non-provisional application Ser. No. 13/024,070 titled "Wireless System for Monitoring and Analysis of Skiing" filled on Sep. 2, 2011, which claims benefit of priority under the 35 U.S.C. section 119 of Provisional Application No. 61/310, 584 titled "Wireless System for Monitoring and Analysis of Skiing" filed Mar. 4, 2010, which are hereby incorporated by reference in its entirety as though fully and completely set forth herein.

FIELD OF THE INVENTION

The present invention relates to the field of monitoring and analyzing skiing activities, and specifically: to monitor the skier body position and forces experienced by his/her body and equipment; to provide new level of safety; and to enhance skiing experience. Such system is based on processing sample data from various MEMS (Micro-Electromechanical System) sensors embedded in the ski equipment and/or skier clothing then calculating moments applied to various parts of the user body and his equipment and to provide corrective feedback to the actuators embedded in the ski equipment. Among other, such corrective action may consist of: changing the tension (extend or shorten) of the ski edge to aid in edge handling; change the torsion of a selected parts of the ski; damping vibration of the ski; and release of the ski bindings when moments applied to the skier leg exceeds safety limits.

BACKGROUND

Currently monitoring of skier/skiing performance relies on few techniques, such as: skier feelings, instructor/coach observations, etc, and some empirical factors, such as: time measurements, post run video analysis, while the safety and comfort depends on decades old ski binding technology, incremental progress in materials and manufacturing technology.

Some analytical methods for data collection during the development phase of the ski equipment are in use today, however, most of those techniques are not practical for the every day training of professional or recreational skier, as they require bulky equipment and require large team of highly skilled technicians to operate.

It is well known that the safety of skiing depends predominantly on ski bindings. Currently, binding safety is defined by the stiffness of it's spring(s) used to hold/release ski boot, which is adjusted according to the presumed capability of the user and the user weight. This basic principle of ski binding didn't changed in past 40 years (also many incremental improvements, such as: multi-pivots/springs were added), and perform satisfactory most of the time—when the speeds are modest, the spring pre-set torque was below the critical level and the user is physically fit, the fundamental problem—relying on intuition for setting the spring strength and fact that in almost all cases, only one of the binding, the one experiencing excessive force, will release. This is mainly to the fact that the forces applied to both skis and/or skis trajectory are not the same. In effect, while one ski is released the other, the other is still attached to the user causing serious injuries during a fall, a major source of trauma to the knee's Anterior Cruciate Ligament (ACL).

This type of injury is induced via a torque mechanism (so called "Phantom Foot"), when the skier looses balance backward while the skis are still turning. While this occurs, a majority of the skier's weight is on the tail of the downhill ski (that is, the ski closest to the base of the ski run). Due to the loss in balance, the skier is unable to turn properly, and momentum keeps his or her body headed down the hill. Unfortunately, the downhill ski is still turning, and continues turning. The turning ski rotates the boot internally, which causes internal rotation of the foot. This in turn rotates the lower leg inward relative to the thigh. This leads to the ACL becoming stretched, then sprained, and if the breaking point is reached, it tears.

Another type of common knee injury referred as "forward falling" occurs when front of the inside edge of one ski starts "dragging" on the snow—this is common when the ski trajectory diverge outwards, causing external tibial rotation, which in combination with forward velocity extends the knee.

Current monitoring systems are not practical for every day use and analysis of the run is lest to subjective interpretation, while the safety of the skiing, provided mainly by the ski bindings, is left virtually unchanged for the past thirty years.

In recent years, the use of mobile devices and, in particular, cellular telephones has proliferated. Today, cellular phone besides providing basic communication over cellular network is equipped with various input/output capabilities, such as wireless PAN (Personal Area Network), and provides significant computing resources. When such computing resources communicate with the remote sensors, such as MEMS accelerometers, magnetometers, gyroscopes, pressure sensors, actuators the resulting system can provide various sport analytical tools for monitoring of skiing.

By coupling MEMS accelerometers and actuators embedded in the ski equipment with an analysis application residing in the user smart-phone, one can provide tool analyzing forces experienced by the user and increase in safety and comfort of skiing. Furthermore, using the smart-phone connectivity to the wireless cellular network, a real-time feedback to the remote location may be provided to add in ski testing or training. System described in this invention can operate using any of wireless technology such as: cdma2000, UMTS, WiMax, LTE. LTE-A, etc.

SUMMARY OF THE INVENTION

This invention allows for the analysis of skiing and remote monitoring of the skier performance. The system consists of a various sensors embedded in the ski equipment or attached to the skier, communicating wirelessly with analysis application residing in the skier smart-phone. The output of the sensors representing instantaneous changes in acceleration in X/Y/Z axis, and in relation to the changes in earth magnetic field provide data for calculation of skier position, moments applied to the ski edges, and forces experiences by the skier body and his equipment.

According to this invention the MEMS motion sensors such as: accelerometers, gyroscopes, magnetometers, barometric pressure and MEMS actuators are embedded in various locations essential for the measurement of skier performance, such as: skis, ski boots, cloth, poles, gloves, etc. Those sensors are sampled at an appropriate rate to provide real-time measurements of moments applied to the ski equipment and skier body.

When such sensors are equipped with the wireless communication link and monitoring application capable of analyzing such data, such system can provide real-time monitoring of skier performance. The results of such analysis can be transmitted over-the-air using mobile terminal wireless interface or can be stored in the mobile terminal memory, then downloaded into computer for further analysis.

The results of such analysis can also be used to predict the trajectory of each ski as calculate ski edge "rolls" across the snow as well as ski vibrations, and how such forces and vibration transfers to the ski bindings and the skier legs. In effect, such system consisting of the analysis application residing in the skier smart-phone and communicating over the Personal Area Network (PAN) radio interface with the actuators embedded in the ski bindings and/or skis may provide new level of safety and comfort by releasing the skis before the forces applied to the skier knees exceed predefined for this particular user safety level and/or dampen excessive ski vibrations.

In addition, such system may equipped with the graphic rendering and capable of retrieving topological information from a radio-telemetry, GPS or GPS synchronized video from slope installed CCTV cameras, such system can display skier position in relation to the slope does allowing for the real-time analysis (by the coach) or post-run review by the user. Both the real-time and post-run analysis provide recording of all parameters of the run, such as edge forces, acceleration, etc, as well as rendering of skier position vs. slope. Furthermore, the graphical representation of the run can be interpolated between the samples to provide a visual representation of the entire run.

BRIEF DESCRIPTION OF THE DRAWINGS

A better understanding of the present invention can be obtained when the following detailed description of the preferred embodiment is considered in conjunction with the following drawings, in which:

FIG. 6 presents the skier body position and monitoring planes vs. ski slope;

Figure 1:
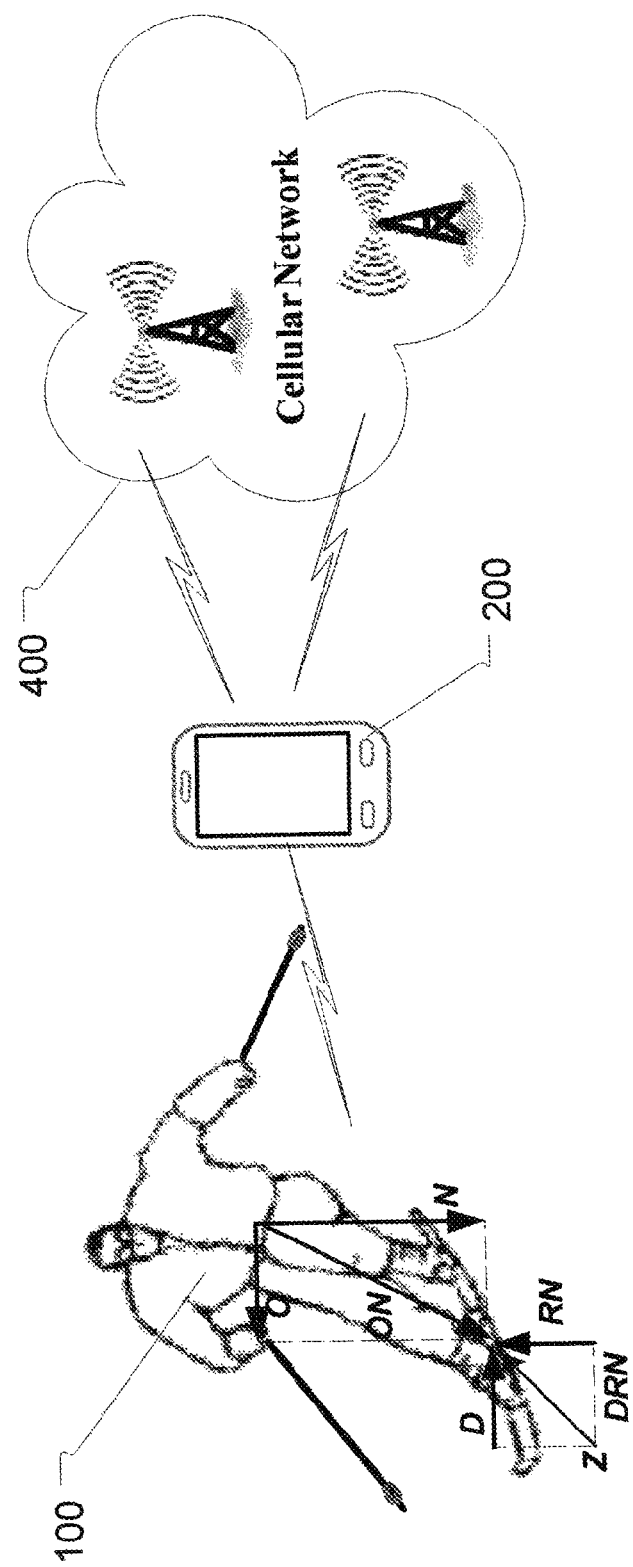
FIG. 1 is an exemplary ski monitoring system.

While the invention is susceptible to various modifications and alternative forms, specific embodiments thereof are shown by way of example in the drawings and are herein described in detail. It should be understood, however, that the drawings and detailed description therefore are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE INVENTION

The following is a glossary of terms used in the present application:

Active Monitoring System—in the context of this invention a system able to collect various instantaneous vectors such as, acceleration, angular orientation, geo-location and orientation, then using various angulation and mathematical operations calculate the forces applied to various areas of sport equipment or the user body then send commands to actuators embedded in the sport equipment to provide corrective action.

Application—the term "application" is intended to have the full breadth of its ordinary meaning. The term "application" includes 1) a software program which may be stored in a memory and is executable by a processor or 2) a hardware configuration program useable for configuring a programmable hardware element.

Coach—in the context of this invention, any person authorized by the user to receive the data from the user monitoring system and provides analysis in real-time or off-line of the user performance.

Computer System—any of various types of computing or processing systems, including mobile terminal, personal computer system (PC), mainframe computer system, workstation, network appliance, Internet appliance, personal digital assistant (PDA), television system, grid computing system, or other device or combinations of devices. In general, the term "computer system" can be broadly defined to encompass any device (or combination of devices) having at least one processor that executes instructions from a memory medium.

Mobile Terminal—in the scope of this invention any wireless MAN enabled terminal such as cell-phone, smart-phone, etc.

Memory Medium—Any of various types of memory devices or storage devices. The term "memory medium" is intended to include an installation medium, e.g., a CD-ROM, floppy disks 104, or tape device; a computer system memory or random access memory such as DRAM, DDR RAM, SRAM, EDO RAM, etc.; or a non-volatile memory such as a magnetic media, e.g., a hard drive, or optical storage. The memory medium may comprise other types of memory as well, or combinations thereof. In addition, the memory medium may be located in a first processor in which the programs are executed, or may be located in a second different processor which connects to the first processor over a network, such as wireless PAN or WMAN network or the Internet. In the latter instance, the second processor may provide program instructions to the first processor for execution. The term "memory medium" may include two or more memory mediums which may reside in different locations, e.g., in different processors that are connected over a network.

PAN—in the scope of this invention, a personal are network radio interface such as: Bluetooth, Near Field Communication (NFC), ZigBee, Body Area Network, etc.

Passive Monitoring System—in the scope of this invention a system able to collect various instantaneous vectors such as, acceleration, angular orientation, geo-location and orientation, then using various angulation and mathematical operations calculate the forces applied to various areas of sport equipment or the user body to provide on-line or off-line analysis of the user performance.

QR-code—Quick Response Code, a 2-D bar code

Ski Equipment—in the context of this invention, any part of equipment used by the skier, such as: skis, ski boots, ski poles, ski clothing, ski glows, etc.

Ski Equipment Parameters—in the context of this invention, ski or snowboard design and manufacturing parameters, such as: length, weight, toe/center/tail, stiffness, are extracted after manufacturing and entered into application.

Software Program—the term "software program" is intended to have the full breadth of its ordinary meaning, and includes any type of program instructions, code, script and/or data, or combinations thereof, that may be stored in a memory medium and executed by a processor. Exemplary software programs include programs written in text-based programming languages, such as C, C++, Visual C, Java, assembly language, etc.; graphical programs (programs written in graphical programming languages); assembly language programs; programs that have been compiled to machine language; scripts; and other types of executable software. A software program may comprise two or more software programs that interoperate in some manner.

Topological Information—in the context of this invention, information about the topology of the ski slop obtained through any combination of techniques such as: topography maps, GPS, Radio-Telemetry, barometric pressure monitoring, etc.

User—in the context of this invention, skier using the monitoring system.

Vibration Control System—in the context of this invention a system able to collect various instantaneous vectors such as, acceleration, angular orientation, etc., then using various mathematical operations calculates resonance frequencies of vibrating ski then sends commands to actuators embedded in the sport equipment to provide corrective action.

WMAN—Wireless Metropolitan Access Network such as cellular network.

Description of Preferred Embodiment

The proposed method leverages on the properties of wireless Personal Area Network (PAN) such as Bluetooth and wireless wide area network, such as a cellular network, and combines the inherent benefits provided by those networks with the sensing technology such as: MEMS accelerometers, gyroscopes, magnetometers, actuators, embedded into skier equipment and an application software residing in the personal wireless terminal (for example user cell-phone).

In this invention sensor technology embedded in various places of the user ski equipment, provides instantaneous measurements of various moments applied to the skier body and his equipment to a mobile terminal based monitoring application over the PAN wireless interface. These measurements in addition to topological and location information (obtained from preloaded slope maps, GPS, Galileo, radio-telemetry, etc.), as well as user physical parameters, such as: weight, heights, distance from ankle to knee and hip, etc, and ski physical parameters, such as: total length, edge length and radius, etc. are used by the monitoring application to provide piece-wise analysis of the user run.

Since the ski edging is created by tipping (inclining) different parts of the skier body: feet/ankles, lover legs/knees, upper legs/hips and lower spine, then by placing sensors in various positions of ski equipment and skier body and then continuously recording the instantaneous changes of acceleration in x, y or z axis, one can reassemble the skier position during his run. Then with additional information about user physical characteristics (weight, heights distance from ankle to knee and hip, etc.), compute forces applied to the ski edge and experienced by the skier body.

Assuming moderate sampling rate of 1 kHz and 100 km/h speed, the exact skier position in regarding to the slope and ski as well as forces he applies to the ski edges and forces his body is experiencing, are calculated every 2.8 cm along the length of his run.

These piece-wise data are interpolated to provide continuous picture of the run and when superimposed over the graphical representation of the user, it provides realistic graphical representation of the run associated with the information obtained during the analysis.

Such graphical representation with corresponding moments may be reviewed in a real-time and transmitted to the coach wireless terminal, who in turn can feed back the advice to the user over the same wireless link or any other means of communication, or may be transmitted over such wireless network to the server for future off-line analysis, or may be stored locally within the monitoring application RAM.

Further improvements are possible when such monitoring/analysis system is augmented with the feedback mechanism providing commands to MEMS actuators placed inside the ski equipment. Such actuators can change the forces applied to the ski edge be extending or contraption of the ski edge length, provide vibration damping mechanism or instantaneous release of the ski/ski boot connection when certain dynamic forces are present.

Figure 2:
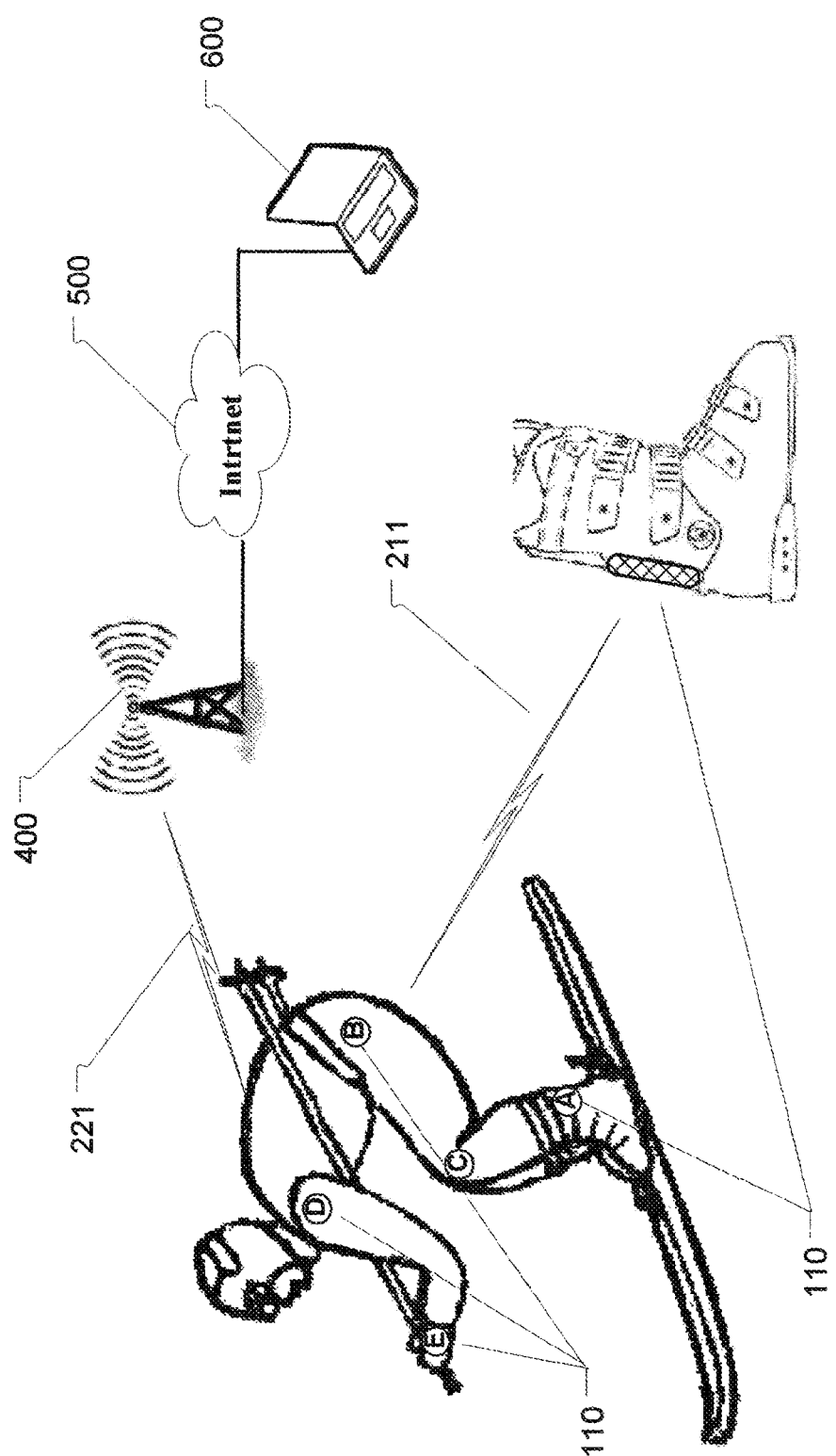
FIG. 2 depicts an exemplary location of the monitoring sensors and communication means.
Figure 3:
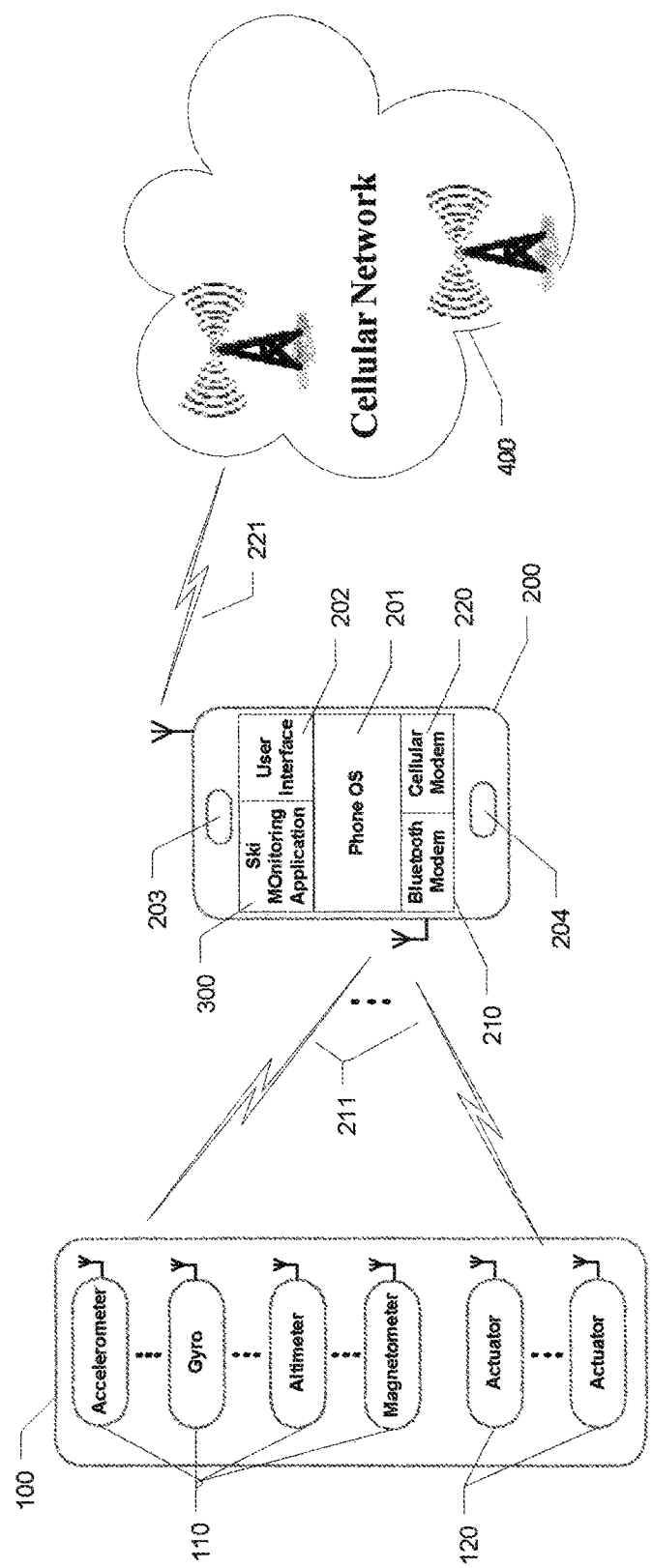
FIG. 3 presents an exemplary architecture of the monitoring system.

An example of such system is presented in FIG. 1 and FIG. 2 and FIG. 3. Here, the monitoring application is embedded into the mobile terminal 200 and communicates with the monitoring subsystem 100 consisting of MEMS sensors 110 and MEMS actuators 120 using short range PAN wireless network 211. The mobile terminal 200 is connected to the analysis application 600 through the wireless MAN link 221 and/or Internet network 500.

Sensor 110 of FIG. 2 such as MEMS accelerometer, gyroscope, magnetometer, altitude-meter, etc. is embedded in various strategic places of the ski equipment and/or skier clothing. Those sensors measure predefined parameters such as accelerations in x/y/z axis, barometric pressure, changes in the earth magnetic field etc. Such measurements are sampled at the predefined for particular application and activity rate (i.e. 5 kHz for professional skier and 500 Hz for recreational skier), then transmitted to monitoring application 300 residing within the mobile terminal 200.

Figure 4:
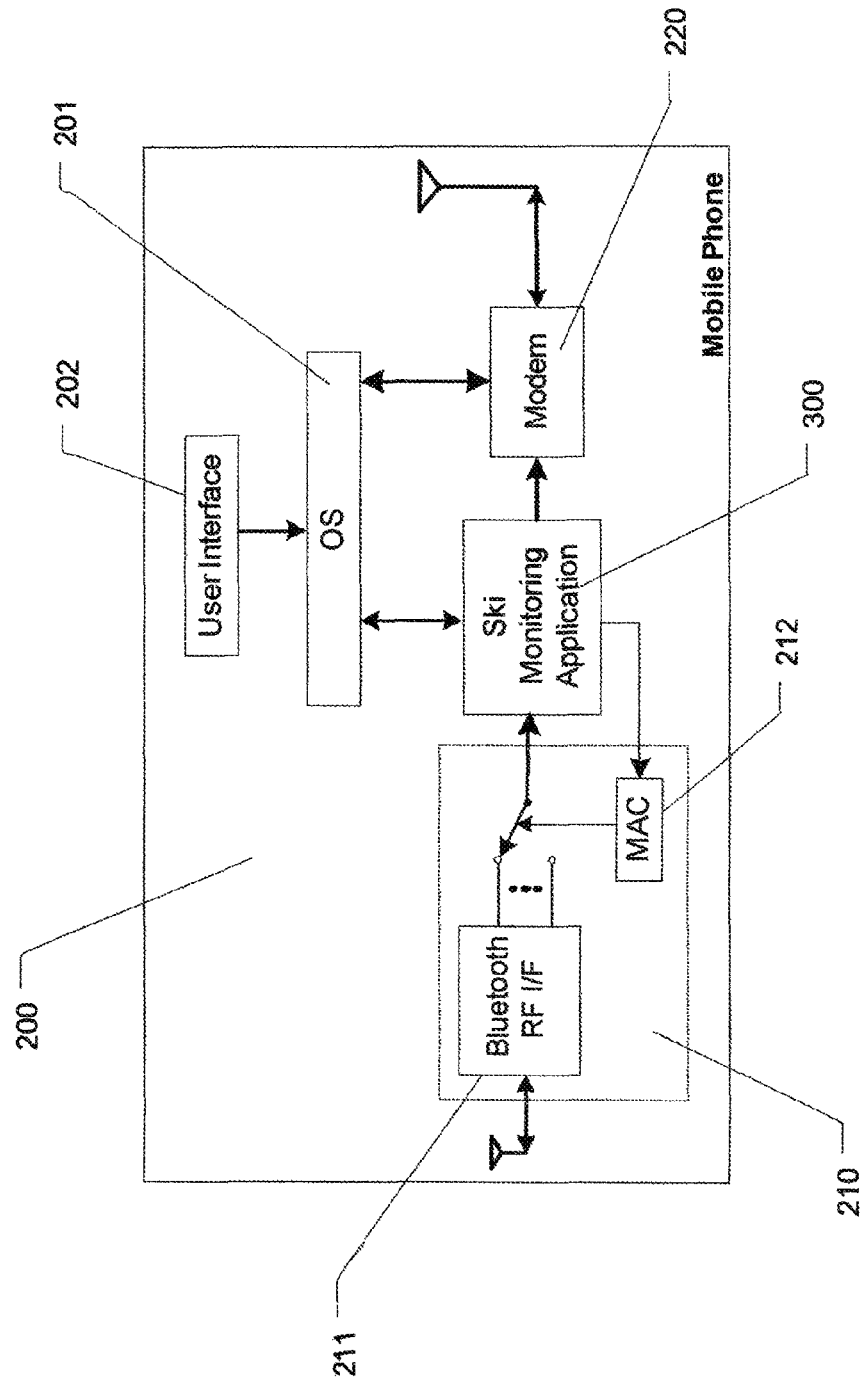
FIG. 4 presents the block diagram of the monitoring application residing within user mobile terminal.

The exemplary monitoring application 300 of FIG. 4 resides within the wireless terminal 200 which consist of short range wireless interface 210, such a Bluetooth, communicating with the sensor/actuator sub-system over wireless link 211 a wireless modem 220 communicating with the MAN network over wireless link 221, a modem OS (Operating System) 201, and the user interface 202.

At the predefined sampling rate the monitoring application 300 sends command to the PAN Media Access Layer (MAC) 211 requesting current measurements. In response the MAC layer retrieves data from each sensor in sensors using RF interface 211, than transfers such data into the monitoring application memory.

Figure 5:
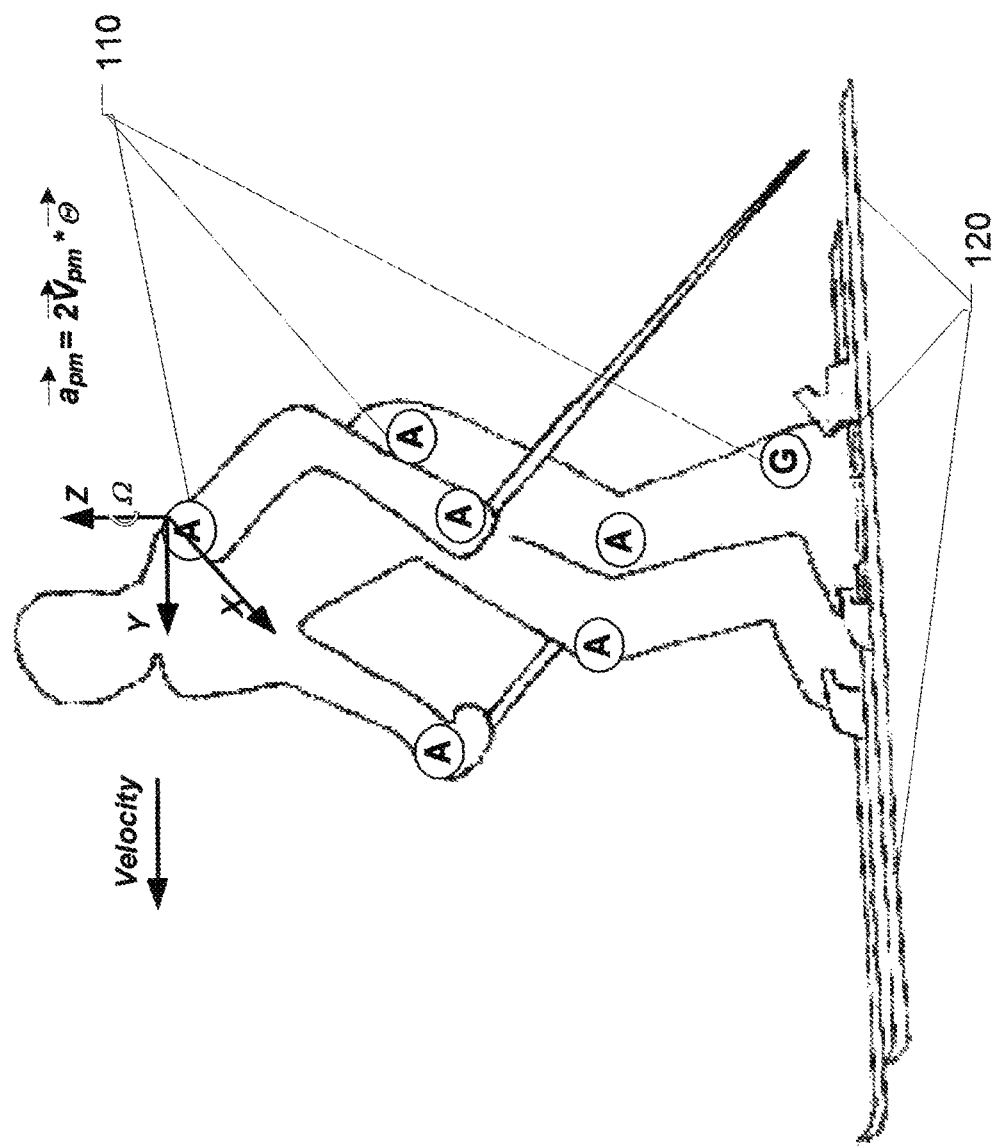
FIG. 5 depicts an example of vectors monitored by various sensors.

Various sensors such as accelerometers, gyroscopes, magnetometers 110, of FIG. 5 are assembled in different configurations to provide measurements of instantaneous vectors in x/y/z axis with 3 or 6 degree of freedom does providing a snap-shot of skier movement. Here the sensors placed on the skier body or embedded into clothing provide information of the position of arms, hips, knees, etc. used to calculate position of skier body vs. the slope line.

FIGS. and 6 presents method used to calculate forces experienced by the skier body. Here data obtained by sensors D-D are used to calculate changes of angle Θ, between skier shoulder plane and the ski slope; data obtained from sensors B-B are used to calculate changes of angle δ, of skier hips in relation the ski slope; data from sensors C-C, to calculate changes in the angle λ, of skier knees vs. the ski slope; and data from sensors A-A, to calculate changes in the angle φ, of skis vs. the ski slope and vs. the other ski. When such results are combined with the user physical characteristics (weight, height, knee-hip distance, etc.), one may calculate forces experienced by skier body, such as: rotational acceleration, centrifugal force, forces applied to the ski edges, as well as distance between ski edge and inner turn hip or distance between inner hip and slope among the others. Such calculations may be performed using well known mathematical methods, among others—angulation.

Results of such calculation may be then presented in a form of data tables or graphs and synchronized to the real-time video of the run or superimposed over graphical representation of the user.

The piece-wise representation is post-processed (interpolation, smoothing, rendering, etc), by the analysis application then the entire run is recreated in graphical form or synchronized to teal-time video with forces presented in form of graphs and tables. Such representations can be stored in the wireless terminal local memory for later use, or transmitted over the wireless network 400 to the remote location 600.

Figure 7:
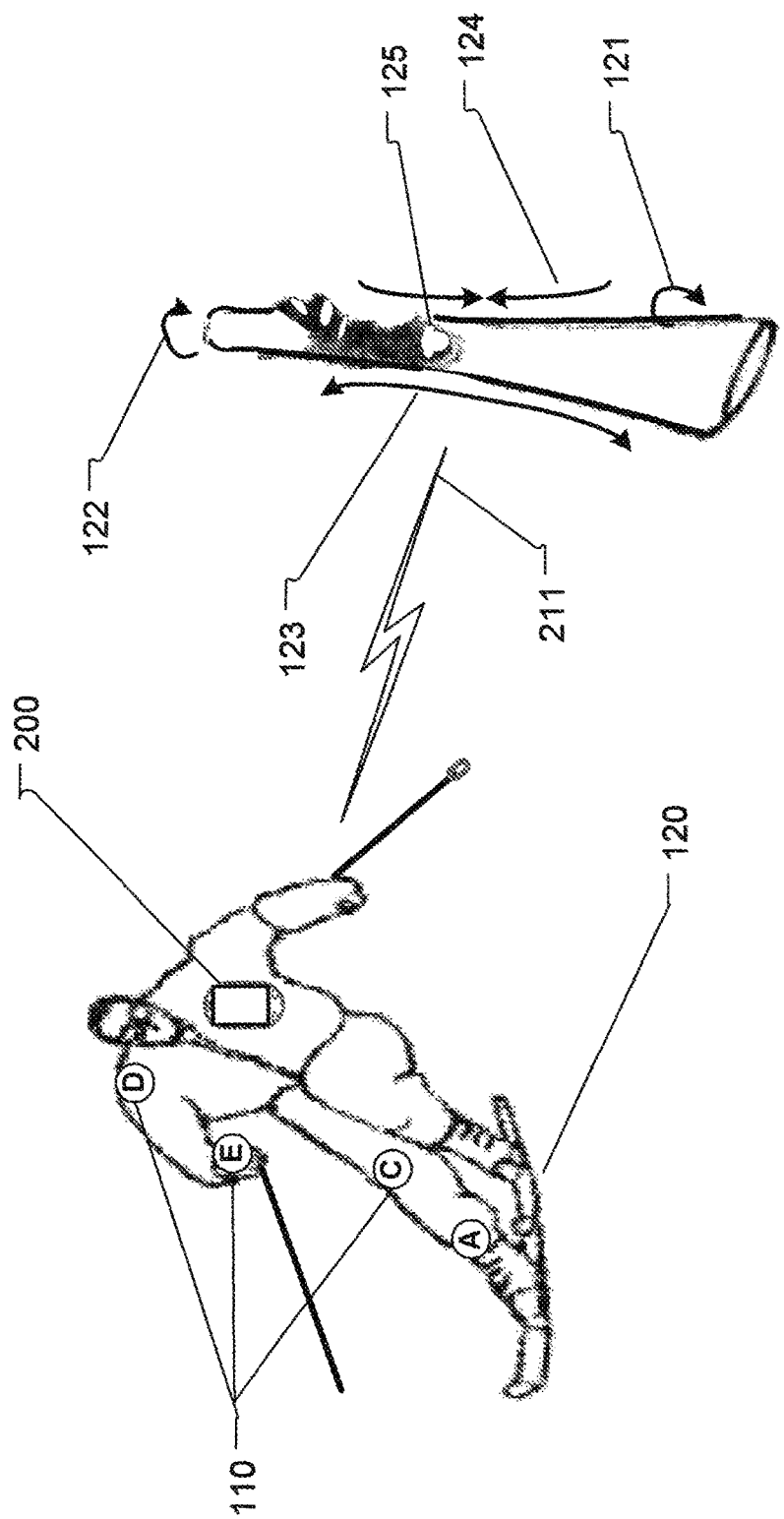
FIG. 7 depicts effects of the active system on the ski.
Figure 8:
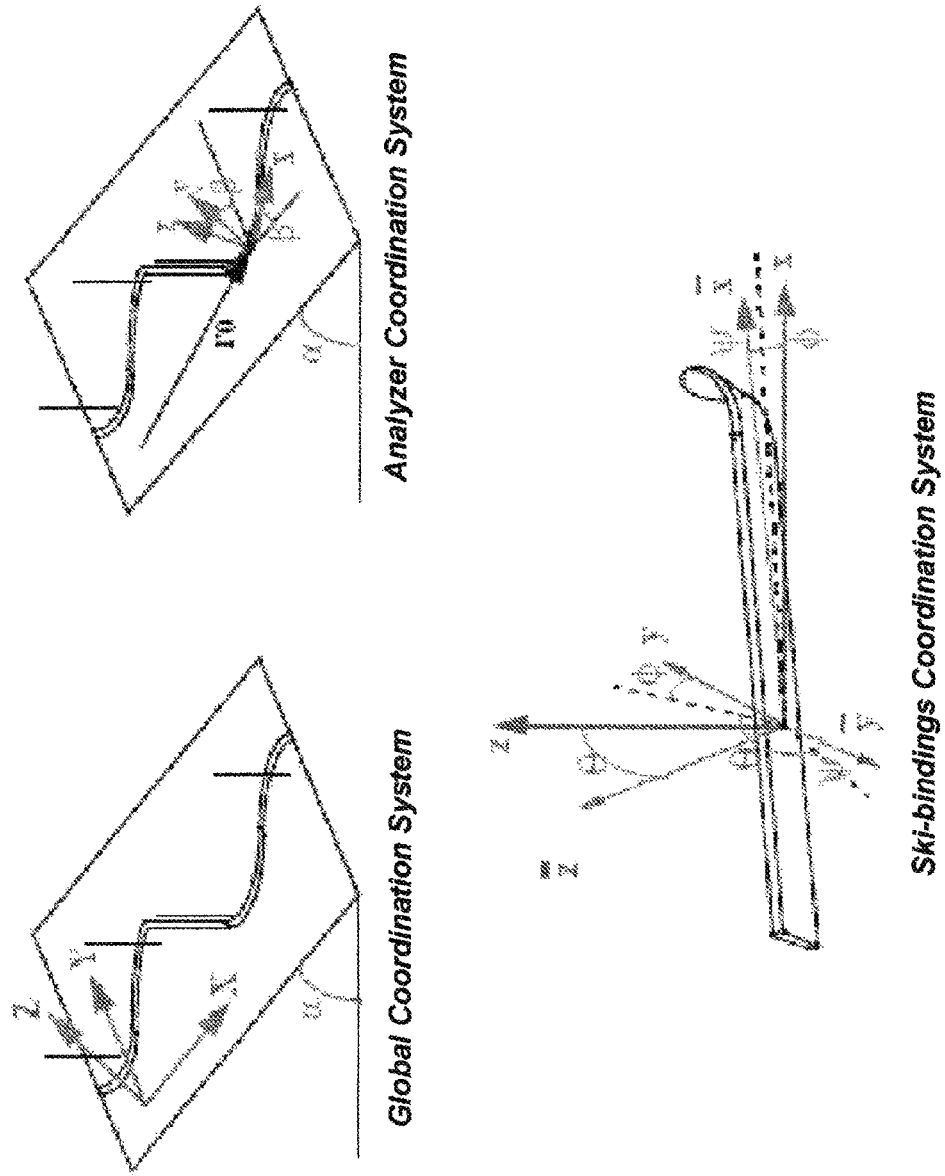
FIG. 8a through 8b, presents the global and local coordination system, while FIG. 8c coordination system attached to the ski-binding system.

FIG. 7, depicts the analysis application operating in an active mode. Here results of the analysis describe in previous section in reference and FIGS. 5 and 6, are convolved by a correction metric, then the resulting corrective commands are send to the MEMS actuators 120 embedded in various places of the ski equipment. Those corrective commands may for example: change the torque of an particular part of the ski 121 and 122; extend the outer (to the turn) edge of the ski 123, while contracting the inner (to the turn) edge of the ski 124, does improving the ski edge contact and turn performance; dampen excessive ski vibrations; or release the ski binding 125 when the forces experienced by the ski/ski-boot interface exceed predefined safety limits.

The safety parameters of ski/ski-boot interface are calculated every sampling period based on user physical parameters and data from sensors, such as speed, moments applied to certain parts of the skier body, moments on the ski edges, relative (to each other and the slope) ski position, etc. When the instantaneous ski/ski-boot interface value exceeds the dynamic safety threshold for any of the skis a release command is sent to both ski bindings, does eliminating the danger of fall with one ski still attached to the skier leg.

To allow full analysis of the run, beside data received from various sensors, other information specific to the user and his equipment, and if applicable—topology of the run, should be provisioned into application memory.

The first such information may contain user physical parameters, for example: user weight, height, ankle to knee distance, ankle to hip distance, hip to shoulder distance, length of the arm, etc. Such parameters are easy obtained by the user and may be entered among the other methods manually through the mobile terminal UI, or through imaging, by scanning of the QR-code of bar-code or an NFC tag attached to skier clothing.

Additional parameters may include location of the sensors, for example: in skis, ski boots, ski bindings, knee, hip, shoulder, elbow, glove, top of the ski poll, etc. as well as distance between some (or all) of them, for example: distance between ski boot and knee sensor, distance between knee and hip sensor, etc. Such information may be entered into the application manually through the UI or obtained automatically or by other means, such as: scanning of the QR-code or an NFC tag attached to ski equipment, radio ranging, differences in barometric pressure, etc.

The second such information may contain physical characteristics of the ski equipment; such as but not limited to: total ski length and weight, length of the ski edge, turning radius, stiffness/elasticity of various parts of the ski (tip/tail/etc.), ski boots and bindings types and settings, etc. Such parameters may be embedded into the QR-code or an NFC tag attached to the equipment. In addition, when the monitoring application operates in the active mode, the location and type and characteristics of MEMS actuators, for example: edge extension/contraction, vibration damping, etc. tables are included. Such parameters may be obtained from the manufacturer supplied in form of encrypted data files, such as QR-code or an NFC tag attached to the equipment. Such data files can be downloaded over the air during application provisioning by scanning of the QR code or an NFC tag.

The third such information may contain the topological parameters of the ski run such as 3D map(s) or topological contours, etc. Such information can be either preloaded to the application from the ski resort website or downloaded over-the-air automatically when the user transfers from one slope to another based on skier location.

The forth information may contain indication if the topology mapping is supported by the GPS (enough visible satellites plus required accuracy), or radio telemetry system installed along the ski slope or time synchronized (GPS, Galileo, etc) slope CCTV cameras, or barometric pressure transmission capability or any combination of the above. Such information may be obtained automatically by the application when the user enters any specific area.

At each sampling period, vectors from the accelerometers 110, together with the first, second, third and forth information are used by the monitoring application to calculate moments applied to various part of the user body as a moments G, N, P, R, etc., then constructs graphical representation of the user superimposed over the slope topography using information and/or a real-time video. This process is visually presented in FIG. 6, with some of the vectors representing the user position. From those vectors, one can calculate moments applied to ski edge RN and knowing the vector DRN (acceleration along the ski radius), calculate the "skid" along vector D. In a practical system, vectors from multiplicity of sensors (skis, knees, hips, shoulders, hands, etc.) are used to obtain the overall representation of the interaction between skier and the slope.

When the system is operating in the active mode as presented in FIG. 7, after the instantaneous vectors are analyzed a corrective metrics is calculated, then a corrective commands are sent to one or multiplicity of MEMS actuators 120 embedded in the ski or ski bindings over wireless link 211. Such command may change the stiffness of the certain part of the ski 121 and 122, or extend 123, or contract 124 ski edge to enhance ski grip during the turn, or damp temporary vibration of certain part of the ski, or trigger the release of the ski binding 125.

Description of Another Embodiment

In this embodiment forces applied to the user legs, in particular his knees, current and predicted trajectories of each ski, vibrations transferred from the ski to the ski bindings are analyzed. The results of such analysis are then scaled by the equipment and user specific information and if any of the safety parameters exceeds one of the predefined thresholds signal releasing bindings of both skis is generated and sent to the actuators embedded in the bindings.

During past three to four decades the concept of alpine ski bindings remained virtually unchanged relying primarily on the torsion applied to one or more springs, and the set of lathes and pivots. Such ski safety system is reliable in operation but have several significant problems: a) the torsion of the release spring is setup intuitively based on "visual" estimation of skier physical parameters and his/her skill estimates; b) when in turn, ski and skier legs are working independently, where each ski and knee experiencing different speed/acceleration and forces.

During an emergency situation, and only if the force applied to the binding exceeds the release spring torsional threshold, only one of the ski bindings will release, while the other will for some time be still attached. So even in the case that the arbitrary setup of the release spring force was correct, the injury to the other leg (not released), is highly probable.

However, if the release spring(s), together with their arbitrary torsion setup is replaced by MEMS thermo-mechanical actuators controlled by the user smart-phone based analysis application, a new level of safety is achieved.

The accelerometers and gyroscopes, 110 provide measurements of acceleration vectors. Such vectors are transmitted to the user smart-phone using PAN wireless interface (such as low power Bluetooth), 211. The analysis application 300 receives samples of xyz vectors at the suitable rate. The received sequence of x[n] samples represents continuous-time domain function x[t], at discrete moments in time t=nT, where T is the sampling interval in seconds, and $f_s=1/T$ is the sampling rate (samples per second), in conjunction with the user physical characteristics stored in the first information, and by the ski equipment parameters stored in the second information and by the calibration parameters are used to calculate moments experienced by the ski equipment and skier body—FIG. 6. Such moments are then classified, compared to the thresholds obtained during bindings calibration and used to generate a control signal which is transmitted over wireless interface 211 to the actuators 125 embedded in the ski bindings.

Functionality of such active binding system may be better understood from FIGS. 8 through 15 and associated description.

First, lets us define the coordination system used by the ski bindings safety analysis application. The acceleration vectors received from the accelerometers are denoted with small letters x, y, z, and related to the motion of the ski on the snow surface (but not to the ski) and is accelerated relative to the global system XYZ. Thus, the x and y axis are rotated in relation to X and Y by an orientation angle β, which is defined by the velocity of the ski:

$$\tan\beta = \frac{v_Y}{v_X}.$$

and is determined separately for each ski. Such coordinate system is presented in FIG. 8.

Another coordinate system which is attached to the ski and denoted as x', y', and z', with the origin of the on the ski axis at the position marked as middle of the ski boot on the top surface of the ski, thus elevated by a distance $z_0$ compared to the origin of x,y,z. Such coordination system is presented in FIG. 8.

Similarly, another coordinate system donated as: x", y", and z", with the origin at the ski axis and elevated by the distance $z_1$ compared to the origin of x,y,z, is attached to the skier knees and used to analyze motion and forces applied to the skier knees. The point of origin of such coordination system is located at points K of FIG. 9.

For each respective coordinate plane, the transformation of the XYZ coordinates into xyz coordinates are performed by rotation of T matrix:

$$T = \begin{bmatrix} 1 & 0 & 0 \\ 0 & \cos\theta & -\sin\theta \\ 0 & \sin\theta & \cos\theta \end{bmatrix}.$$

With respect to the external coordinate system XYZ the ski binding system has five degrees of freedom: three degrees of translation and two degrees of rotation. The rotational degrees of freedom are a rotation with the orientation angle β around the z-axis and the rotation with the edging angle Θ around the x-axis. The rotational motion on the ski position $r_{ski}(t)$ transferred to the ski-binding system is determined in the external reference system. The velocity $v_{ski}(t)$ and the acceleration $a_{ski}(t)$ in the external frame of reference can then be determined by differentiation. And the acceleration of the ski as a function of the external forces, $F_{iext}(t)$, acting on the ski-binding system of mass m is defined as:

$$ma_{ski}(t) = \Sigma_i F_i^{ext}(t)$$

During run, the three main external forces acting on the system are: the forces Σtransferred from the user onto the binding, $F_{user}(t)$, the forces acting at the ski-snow interface, $F_{SSI}(t)$, and the gravitational forces $G_{ski}(t)$.

$$\Sigma_i F_i^{est}(t) = F_{user}(t) + F_{SSI}(t) + G_{ski}(t)$$

During analysis, forces and the acceleration are expressed in the frame of reference of the xyz coordinate system, which accelerates and rotates with the angular velocity $\sqrt{} = d/dt\, \beta$ around the z-axis with respect to the external XYZ reference frame. Therefore, any point P at position r, with a velocity $v_r$ and an acceleration $a_r$ relative to the origin o of system xyz experiences additional accelerations due to the rotation of the system.

The forces applied to the ski edge are derived directly from an forward kneeling along the ski axis (x axis), since the skier lower leg is attached to the ski binding and all inner (y axis). However, since the knee operates with the three degree of freedom, the forces transferred from the edge and the rotational forces, create three sets of forces and moments that may exerted upon the knee, such as: anterior forces; external and internal rotation of the lower leg (tibia), which can cause the injury of ACL; outward (valgus) moments, which can cause separation of the medial section of the knee; and inward (varus) moments which can cause separation of the lateral section of the knee.

Figure 9:
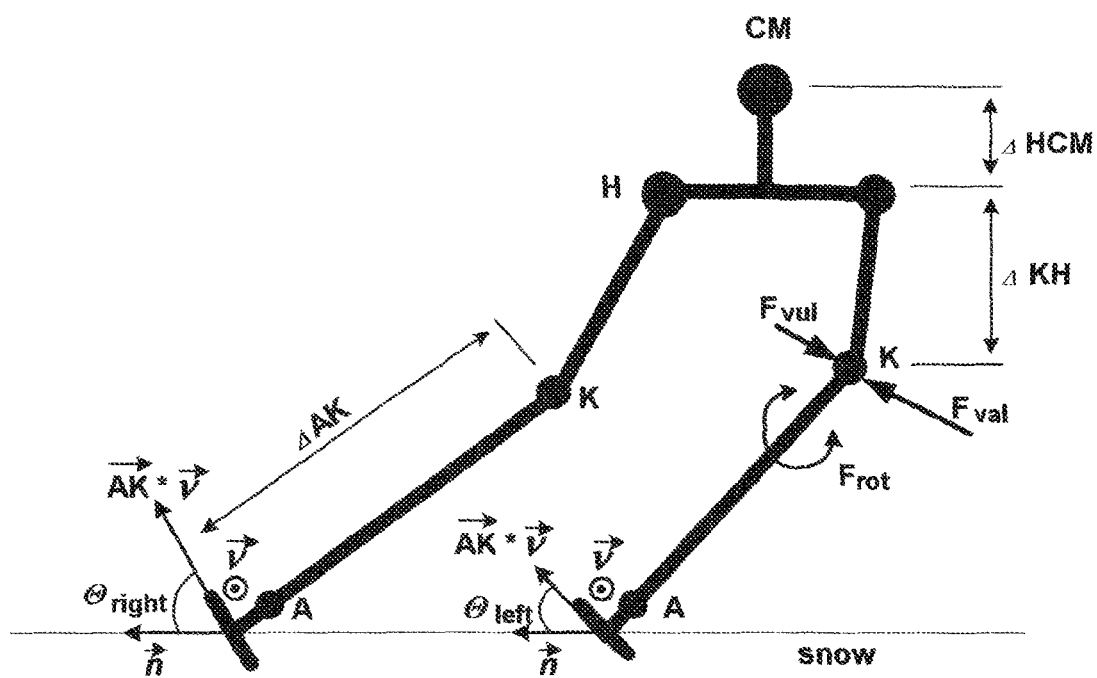
FIG. 9 presents the model of the lower part of the skier body as used to calculate forces and moments applied to the ski-bindings and to the skier knees.

As the skier lower leg is attached to the ski binding and all inner (y axis) forces are directly transferred to the ski edge, there is only one degree of freedom—forward kneeling along the ski axis. As such angulation analysis may assume that the lower part of the ski is part of the plane defined by the ski axis, as illustrated in FIG. 9.

Here the position of the lower leg is determined by the straight line between the skier's ankle A and the skier's knee K. The cross product of the straight line AK, defined by the knee and ankle positions, with the skiers trajectory v is a vector perpendicular to the ski axis and parallel to the undersurface of the ski, Θ is the edging angle of the ski on the ski slope, ΔAK is the distance between the ankle and the knee, ΔKH is the distance between the knee and the hip, and ΔHCM is the distance between the hip and the skier CM.

Within the observation interval, the ski-binding system is accelerated and rotates around the z-axis with the angular velocity $\bar{\omega} = d/dt\ \beta$. And around the x-axis in order to increase the ski's edging angle, with the angular velocity $\bar{\omega}_\Theta = d/dt\ \Theta$. The acceleration components represents the inertia forces $F_{inertia}(t)$, which directly act on ski and binding.

The results of analysis of various moments experienced by the ski binding subsystem are presented in graphical form in FIGS. 10 through 13 (Note: the change in algebraic sign occurs when the skier crosses the slope fall line and does not applies negative values of the vectors). Such moments are used to calculate forces applied to the ski binding and skier knees: a) force transferred form the user $F_{user}(t)$; b) force of the ski-snow interaction $F_{SSf}(t)$; c) gravitational force G; d) the inertia force $F_{inertia}(t)$. Furthermore, the time-domain analysis of such moments during the calibration run allow us to define the safety criteria optimal for each individual skier.

Figure 10:
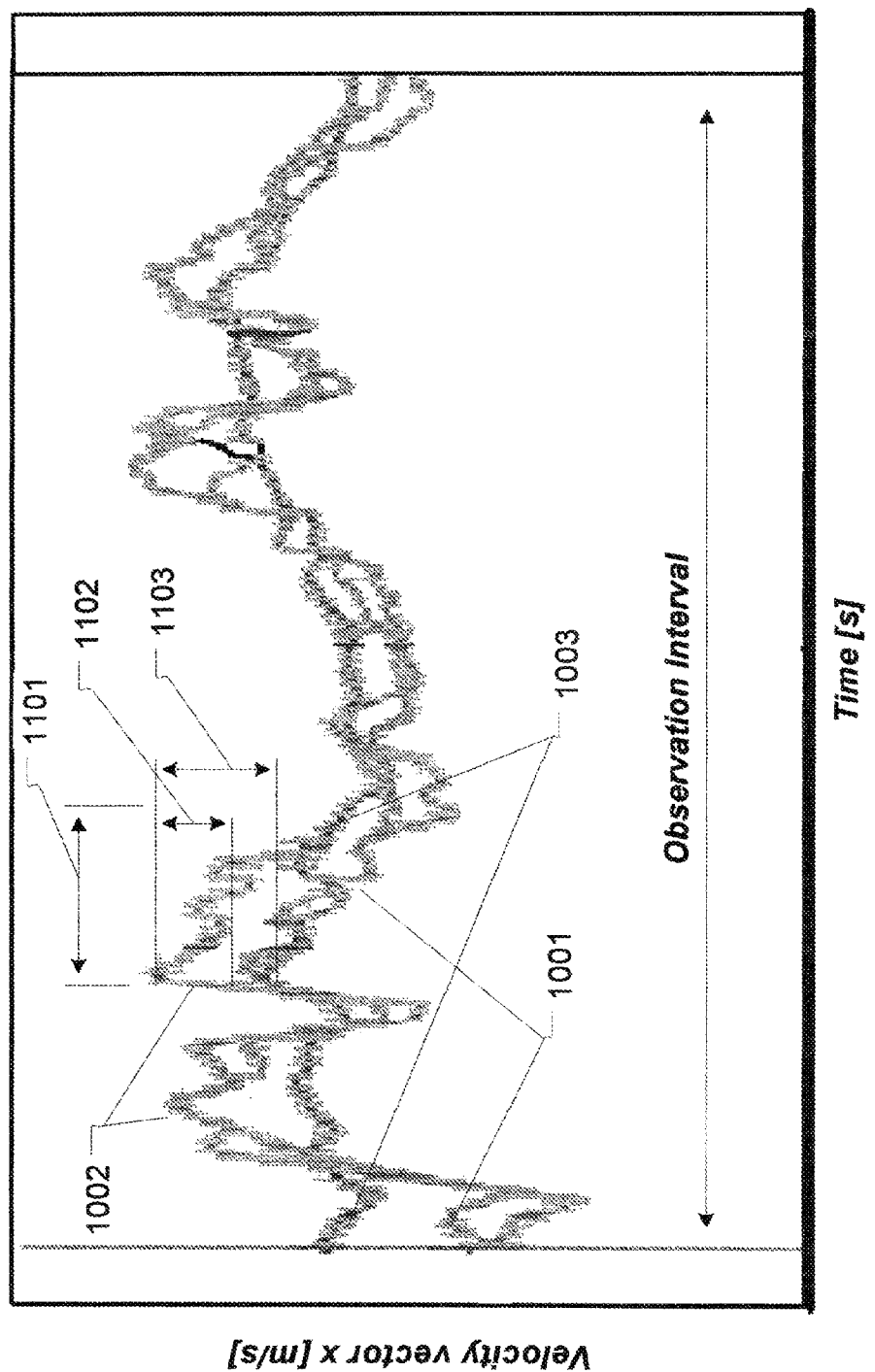
FIG. 10 presents measurements of skier knees velocity in x-axis.
Figure 11:
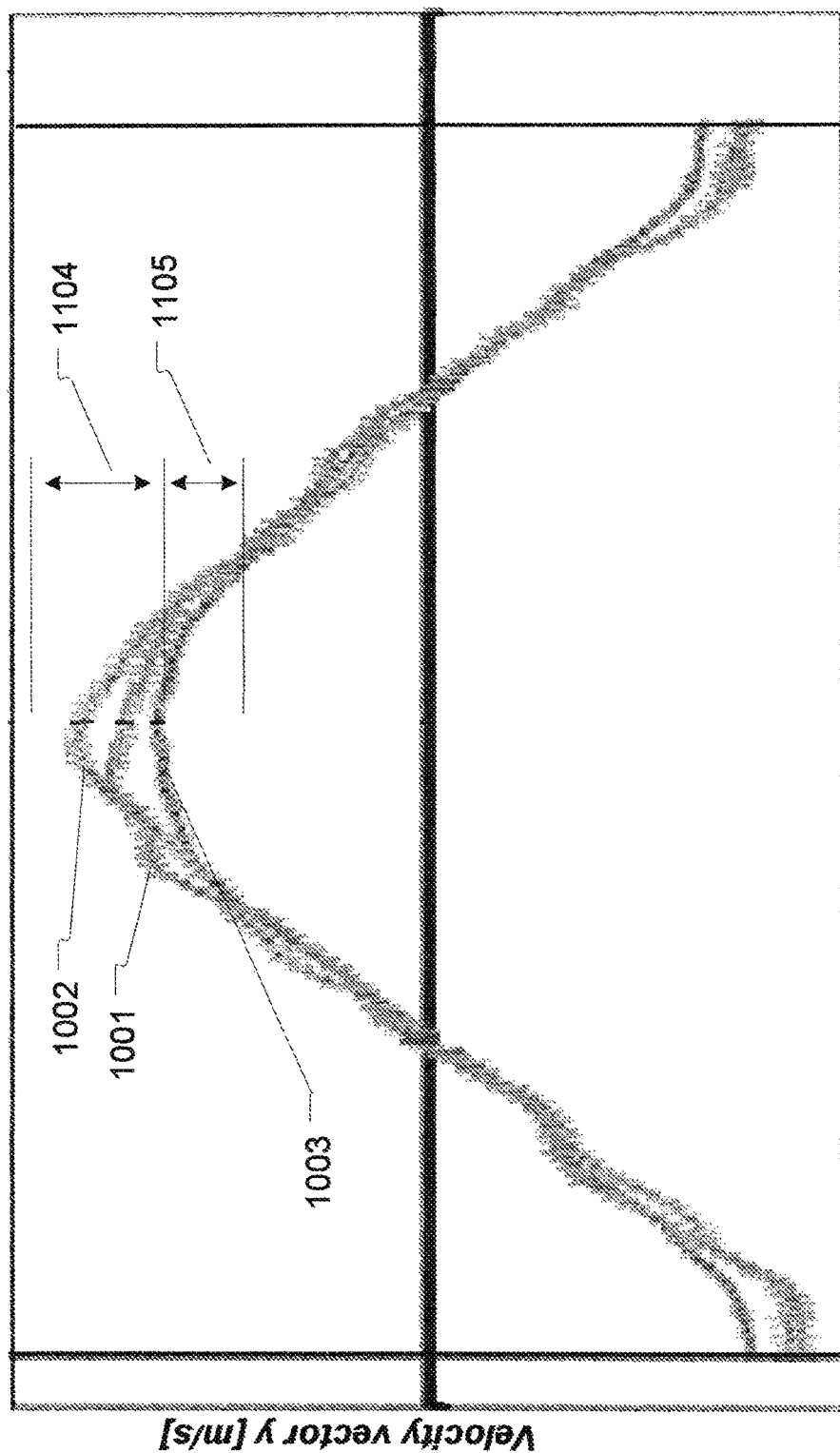
FIG. 11 presents measurements of skier knees velocity in y-axis.
Figure 12:
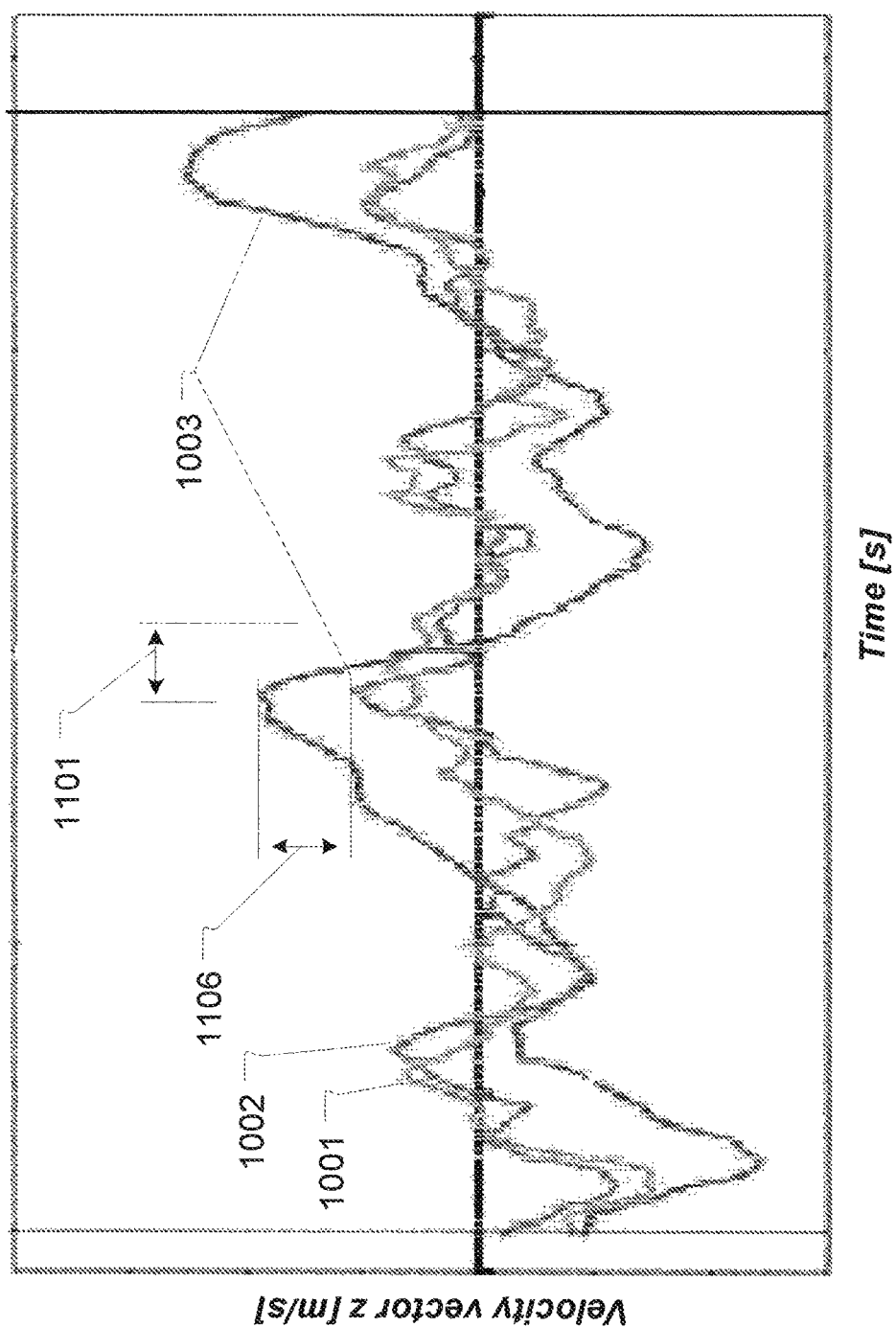
FIG. 12 presents measurements of skier knees velocity in z-axis.
Figure 13:
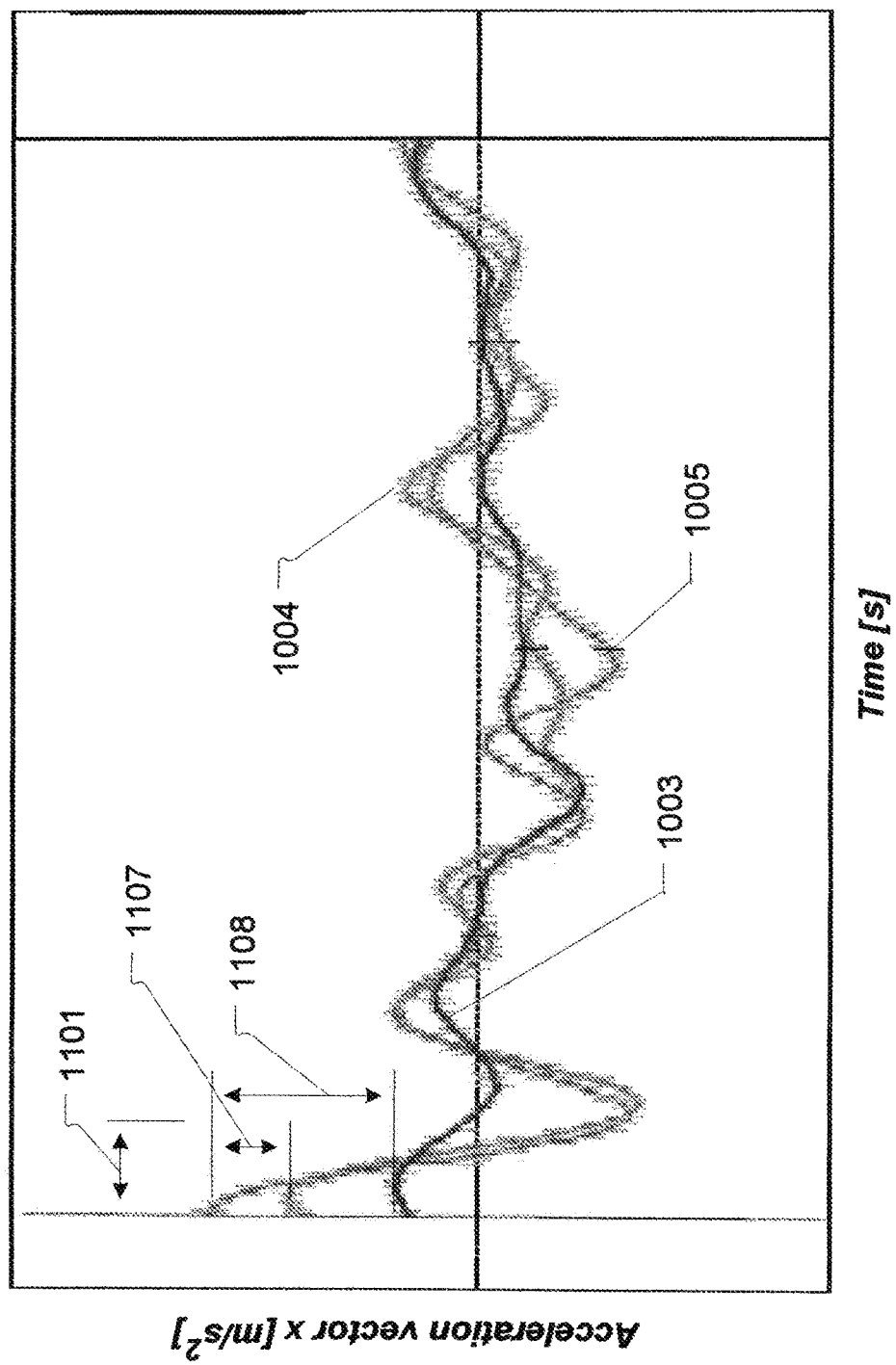
FIG. 13 presents measurements of ski acceleration.
Figure 14:
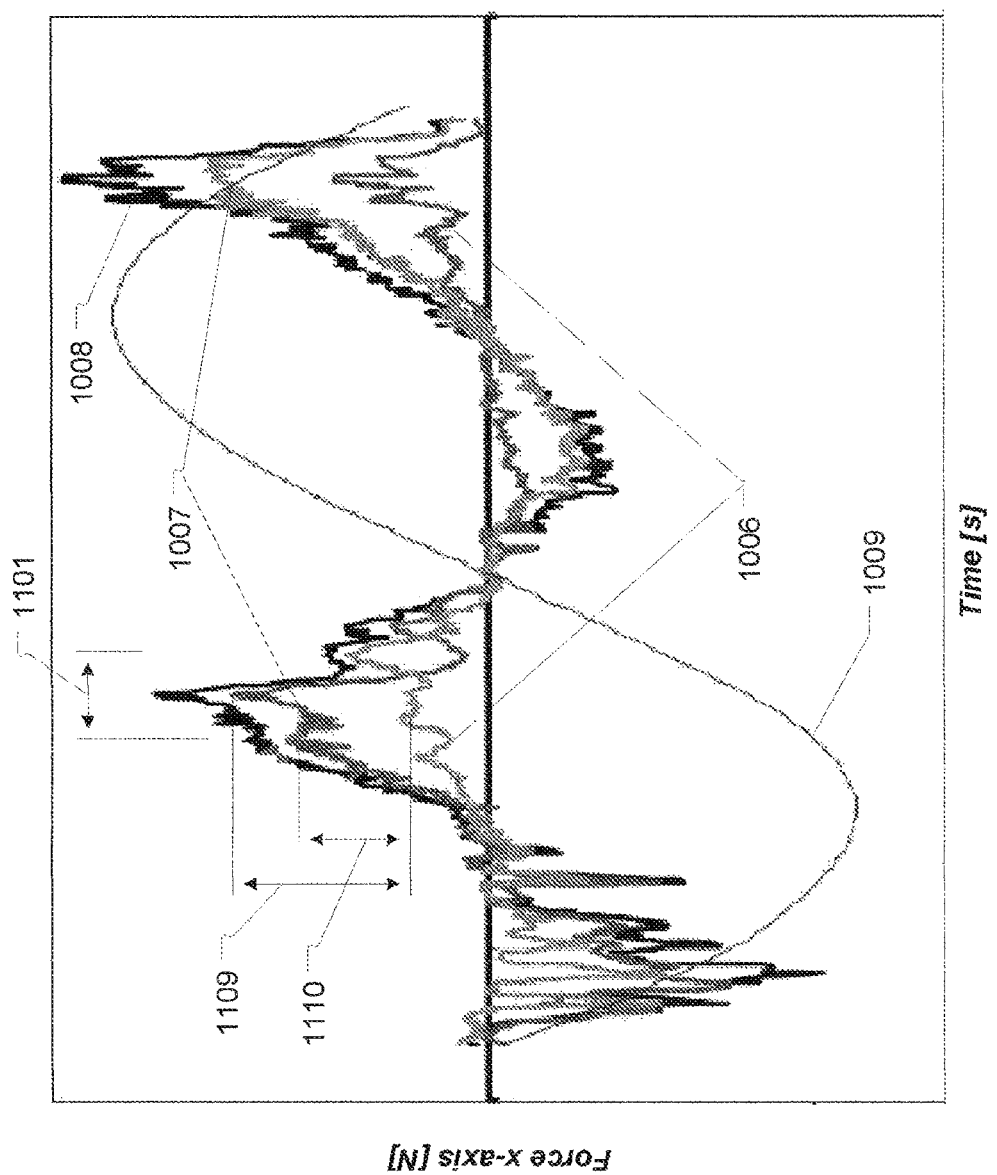
FIG. 14 presents the resulting forces applied to the ski bindings.

First let's observe the results presented in FIGS. 10 through 14, and define the bindings safety criteria in terms of velocity—FIGS. 10 through 12; the angular acceleration criteria, FIG. 13. These measurements in conjunction with the knowledge of skier body position and his physical characteristics provides input for calculation of forces applied to ski bindings, FIG. 14, and to the skier knees.

As skiing must be safe even at low or no velocity—for example when the skier is standing on a slope with skis attached, the adaptive ski bindings must provide safety is such situations as well. This is achieved by analyzing a shock, which is a form of acceleration with is a nonperiodic function that occurs instantaneously, and typically happens only once. Shock, can be determined by performing well know to those skilled in art frequency domain analysis of the time domain samples received from the accelerometers, then applying appropriate threshold to the detected shock signal amplitude.

In FIG. 10, the instantaneous and filtered (solid lines), velocity of the skier Center Mass (CM), 1003, and left 1001 and right 1002, ankle in the X coordinate are plotted versus the time. To remove the variance of the instantaneous acceleration vectors a single pole IIR filter—or any appropriate processing well known to those skilled in art, is applied. It may be observed, that in normal, not emergency conditions: 1) velocity of the outer knee is always larger then the inner knee; 2) the difference in the knees velocity is small; 3) velocity of skier CM is always smaller then knees.

In FIG. 11, velocities of the same run in the Y coordinate are plotted. Here, the velocity of both ankles 1001 and 1002; and the velocity of CM 1003, are similar, except for the mid part of the turn. The larger velocity of the skier, the larger the difference, however, the difference is bounded by the distance between $Z_0$ and the CM.

In FIG. 12, velocities of the same run in Z coordinate are plotted. Here we see that starting from the mid part of the turn velocity of CM is larger then the acceleration of the knees or the ski, while it is similar when the skier traverses the slope fall line.

In FIG. 13, instantaneous and filtered (solid lines) of angular acceleration of skier CM 1003, the left 1004, and right 1005 skis are plotted versus time. Again, in the mid turn, the acceleration of the outer ski is larger while between the turns, acceleration of both skis is similar, and very close to the acceleration of the skier CM. In addition the acceleration of the skier CM is relatively constant while the acceleration of the ankles varies strongly. Furthermore, for non-emergency turn the angular acceleration of the skis is the same, while the acceleration of the skier's CM, which is shifter during the beginning of the turn is slightly smaller.

The value of angular acceleration may be obtained using $2^{nd}$ differentiation of the ski orientation angle. Furthermore, the instantaneous vectors of the ski orientation angle may be used to determine the present and predict the future trajectories of each ski. By accumulating the changes in ski orientation angle β, and the edging angle Θ over the observation interval $T_{observation}$ we obtain trajectory of the skis. This function may be performed using simple integrate-and-dump approach with the integration period having inverse proportion to the velocity or acceleration.

The piece-wise measurement of velocity and acceleration vectors in xyz coordinates is used by the analysis application to calculate the forces applied to the ski bindings. Graphical results of such analysis is presented in FIG. 14 in reference to the skier CM position 1009 versus an y coordinate. Here we see that forces are dominated by the centrifugal force (x-axis), and depend on angle β, which changes from negative to positive value during the left turn and from positive to negative during the right turn, while between turns, when the skier shifts his weight β assumes maximum value. Furthermore, during the turn the centrifugal force increases the load on the outer ski 1009 while decreases the load from the inner ski 1010, and the maximum load is reached when the ski passed the slope fall line. Another component of such analysis is calculation of the forces (load) in z-axis, as such force compresses the skier while transferred through his knees to the snow surface. This is most critical between the turns when the skier rises his body to exert additional force to the grand unloading the skis and shifts his weight on the other edges. The effect of The safety of the ski bindings according to the current invention is provided by: applying various thresholds and timers to the output of the previously described results; applying rules derived from the previously described observations; and scaling the results by the skier physical characteristics, and the results of calibration before applying such results to the binding release actuators. Such thresholds and timers can be used independently or jointly, or additional thresholds/timers may be added without deviating significantly from the teaching of this invention.

First, we assign two thresholds for the each of xyx axis of ski-binding system: velocity 1102 defining the maximum difference between the inner and outer ski, and 1103 defining the maximum difference between the outer ski and the skier CM, in the x coordinate. Similarly 1104, and 1105 define such maximum difference for the y coordinate and 1106 in the z coordinate; while thresholds 1107, and 1108 define such maximum differences for the acceleration vectors in the x coordinate; and thresholds 1109, and 1110 define maximum thresholds for the forces in the x coordinate. Then we assign time observation period within which the comparison of such thresholds is performed, for example, if the acceleration of one of the skis exceeds the predefined threshold, the $T_{trigger}$ 1101 is started during which time, the acceleration of inner and outer ski is compared versus 1002 thresholds and outer ski acceleration is compared with the 1103 threshold. Assuming at least one of the other criteria, such as x, y, or z force also exceeds the predefined threshold, control signal releasing both bindings will be send to actuators embedded in the bindings.

To provide an optimal safety regardless of the equipment parameters, the user physical characteristics and condition, or his level of expertise, the adaptive binding system is calibrated. Such calibration must be performed at least once during the first association of the user smart-phone with the adaptive ski binding system.

Figure 15:
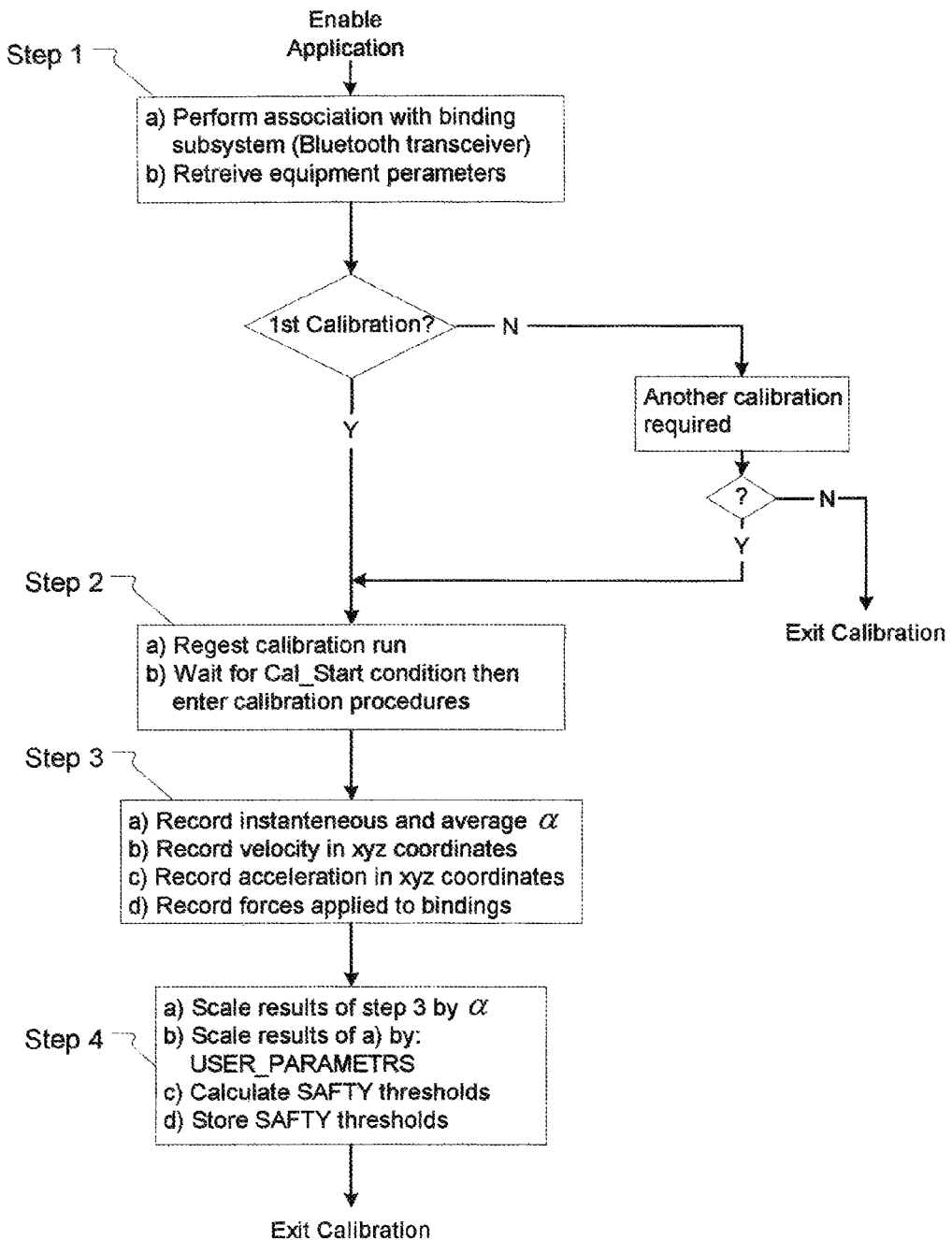
FIG. 15 presents the bindings safety criteria calibration procedures.

The calibration procedures are presented in FIG. 15 and described in details in the following sections. As previously mentioned the skier physical characteristics such as: weight, height, distance from a knee to an ankle, etc. are contained within the first information. Some of the first information parameters, such as: weight, heights are entered into the analysis application by the user through the smart-phone UI, other, such as distance from knee to ankle, hip, etc. may be entered either through the UI or if the sensors are embedded into the ski clothing, by scanning of a QR-code or the NFC tag. The equipment specific parameters, such as type, length, etc. of the ski and ski binding specific parameters, such as distance from the ski top surface to the bottom of the boot sole, height of the ski boot (distance to the ankle), etc. are embedded into the QR-code or NFC tag attached to the ski. As such these parameters are simple entered to the by scanning of the code or the tag.

In Step 1 of calibration, the ski-binding system is associated with the analysis application—application is enable and detects the associated Bluetooth transceiver embedded in the ski bindings, then retrieves the equipment and user information.

In Step 2 analyzer communicates with the user through the smart-hone UI regarding calibration of ski-binding system. In case the association between analyzer and the ski-binding system is done for the first time, calibration is mandatory, while in case, initial calibration was already performed, analyzer will offer new calibration. This "new" calibration may be beneficial as skiing conditions may change from day to day or even from one run to another, for example slight changes in the binding safety profile to accommodating different snow conditions, or type of skiing (race vs. recreation).

In Step 3 analyzer records velocity and acceleration vectors in xyz coordinates, then calculates the moment and forces applied to the ski bindings, and normalize the results by the slope decline angle α.

In Step 4 analyzer retrieves user physical information—weight, height, distance: ankle to knee ΔAK; knee to hip ΔKH; and based on this info and user weight and height calculates the hip to the center of mass (CM) distance ΔHCM, then the forces recorded for xyz coordinate are transposed to x'y'z' coordinate (user knees). Now safety thresholds 1102 through 1110, and 1102' through 1110' are calculated and recorded. While the knee safety thresholds (1102' through 1110') can't be modified, the thresholds 1102 through 1110 may be scaled by the by the user through the smart-phone UI in order to provide slight changes to the bindings characteristic and to accommodate to changing requirements—for example from recreational run to race.

Although the embodiments above have been described in considerable detail, numerous variations and modifications will become apparent to those skilled in the art once the above disclosure is fully appreciated. It is intended that the following claims be interpreted to embrace all such variations and modifications.

We claim:

1. A system to adaptively control the release of a ski bindings comprising:
    a MEMS accelerometers attached to the skier body and embedded into the ski bindings providing measurements of the skier and equipment acceleration vectors;
    a smart-phone based safety analysis system designed to estimate forces applied to the ski binding and the skier knees and to provide control signal to the MEMS actuators embedded in the ski bindings;
    a MEMS actuator embedded in the ski bindings and intended for transferring control signals generated by the smart-phone based safety analysis system into bindings release motion; and
    a radio interface for transferring measurements and control signals between the sensor, a smart-phone based safety analyzer and bindings actuators, and
wherein such safety analysis comprises of:
    at the specified intervals, retrieving an instantaneous acceleration vectors of each of the xyz coordinates from the accelerometers embedded in the ski bindings;
    applying an IIR filtering to the instantaneous acceleration vectors then performing piece-wise estimation of the acceleration, velocity and rotational moments;
    based on such piece wise estimation, and the equipment parameters contained within the second information, calculate forces applied to the ski-binding system for each of the xyz coordinates;
    based on acceleration vectors received from the accelerometers and the skier and ski equipment parameters contained in the first and the second information;
    based on the skier parameters contained within the first information, and the forces applied to the ski bindings, calculate forces and moments applied to the skier knees; and
wherein, the instantaneous forces applied to the ski bindings and the skier knees are compared of with the safety thresholds obtained during the calibration, and if any of such force exceeds the safety thresholds for the time longer then the predefined during the calibration, proved an instantaneously release both bindings by sending control signal to the actuators.

2. The method of claim 1, wherein the MEMS accelerometers and the MEMS actuators embedded into the ski bindings communicates with the smart-phone based safety analyzer using Personal Area Network radio interface.

3. The method of claim 1, wherein the MEMS accelerometer embedded in the ski bindings provides measurements of acceleration vectors in xyz coordinate system.

4. The method of claim 1, wherein the MEMS actuator embedded in the ski bindings is capable of producing displacement with the force required for releasing of the ski bindings.

5. The method of claim 1, wherein the instantaneous acceleration vectors received from the actuators are first filtered using an IIR filter to remove the measurement variance.

6. The method of claim 1, wherein such analysis is performed in time or frequency domains.

7. The method of claim 1, wherein the safety criteria are verified by application of the one or more thresholds to each of acceleration, velocity, rotation and forces, in xyz coordination system for a predefined time duration, before the results of such verification is used to determine bindings release condition.

8. The method of claim 7, wherein one of such thresholds is the difference between the amplitude of the skier center mass and one of the ski or one of the knees, and the other is the difference between one ski and the other ski or one ankle and the other ankle.

9. The method of claim 8, wherein such thresholds are applied independently to each of the xyz coordinates of acceleration, velocity, rotation, or force safety component criteria.

10. The method of claim 8, wherein such thresholds are applied jointly to the xyz coordinates of acceleration, velocity, rotation, or force safety component criteria.

11. The method of claim 8, wherein such thresholds are applied jointly to acceleration, velocity, rotation and force to derive safety component criteria.

12. The method of claim 7, wherein in the absence of velocity, the only the measurement of shock force applied to the ski bindings or a rotational moment applied to the skier ankle is used as a condition for binding release.

13. The method of claim 7, wherein the safety timer is triggered when one of the safety thresholds is exceeded.

14. A method to calibrate adaptive ski binding system comprising of:
   associating the ski binding safety analyzer with the ski-binding system;
   retrieving the equipment parameters from the content of the first information;
   retrieving the user parameters from the content of the second information;
   instructing the user to perform calibration run; and
   wherein during such calibration run, the ski binding safety analyzer records the acceleration, velocity and rotational vectors, then calculates the forces applied to the ski bindings; and wherein after the results of such calculation is scaled by the measurement of the ski slope decline and by the user parameters retrieved form the second information, are stored as the ski binding safety criteria.

15. The method of claim 14, wherein the equipment parameters contained within the first information among the others includes such information as: total length, effective length, turning radius, longitudal and torsional stiffness.

16. The method of claim 14, wherein the user parameters contained within the first information among the others includes such information as: the user weight, height, ankle to knee length, knee to hip length, the distance from the hip to the user center of mass, and the snow condition.

17. A non-transitory computer accessible memory medium for storing program instruction pertaining to the ski bindings safety system, wherein the program instructions execute all of the following:
   retrieve magnitudes and amplitudes of an acceleration vectors from the multi-axes accelerometer using short-range wireless link;
   perform analysis of such acceleration vector in order to estimate forces applied to the ski-binding system, and use such results to obtain ski binding safety criteria;
   scaling of the results of forces applied to ski bindings by the user physical parameters and use such results to obtain skier knee safety criteria;
   compare such ski bindings safety criteria and the skier knee safety criteria with the respective safety thresholds; and
   wherein if any of the forces exceeds any of the safety criteria, generates control signal for the actuators embedded in the ski bindings instructing bindings release.

* * * * *